United States Patent [19]

Jautelat et al.

[11] 4,325,873
[45] Apr. 20, 1982

[54] PROCESS FOR THE PREPARATION OF STYRYL-CYCLOPROPANECARBOXYLIC ACID ESTERS AND INTERMEDIATE PRODUCTS FOR THIS PROCESS

[75] Inventors: Manfred Jautelat, Burscheid; Dieter Arlt, Cologne; Reinhard Lantzsch, Leverkusen; Rainer Fuchs, Wuppertal; Hans-Jochem Riebel, Wuppertal; Rolf Schröder, Wuppertal; Horst Harnisch, Much, all of Fed. Rep. of Germany

[73] Assignee: Bayer Aktiengesellschaft, Leverkusen, Fed. Rep. of Germany

[21] Appl. No.: 138,044

[22] Filed: Apr. 7, 1980

[30] Foreign Application Priority Data

Apr. 23, 1979 [DE] Fed. Rep. of Germany ....... 2916375

[51] Int. Cl.$^3$ ................. C07D 325/00; C07D 317/44; C07C 121/60; C07C 51/58
[52] U.S. Cl. ............................ 260/338; 260/340.5 R; 260/343.6; 260/465 D; 260/544 D; 260/544 S; 560/17; 560/62
[58] Field of Search ................................. 560/17, 62; 260/340.5 R, 544 D, 544 S, 465 D

[56] References Cited

U.S. PATENT DOCUMENTS

| 3,120,551 | 2/1964 | Goldschmidt | 260/544 D |
|---|---|---|---|
| 3,213,072 | 10/1965 | Hoffemberg et al. | 560/62 |
| 4,016,179 | 4/1977 | Fujimoto et al. | 260/465 D |
| 4,157,447 | 6/1979 | Engel | 560/8 |
| 4,161,535 | 7/1979 | Meyer et al. | 260/544 D |
| 4,199,595 | 4/1980 | Berkelhammer et al. | 260/544 S |
| 4,201,787 | 5/1980 | Katsuda et al. | 560/62 |
| 4,204,071 | 5/1980 | Anderson et al. | 260/465 D |
| 4,227,015 | 10/1980 | Collins | 560/62 |

FOREIGN PATENT DOCUMENTS

| 2539895 | 3/1976 | Fed. Rep. of Germany . |
|---|---|---|
| 2706184 | 8/1977 | Fed. Rep. of Germany . |
| 2738150 | 3/1978 | Fed. Rep. of Germany . |
| 2750182 | 5/1978 | Fed. Rep. of Germany . |
| 2800073 | 7/1978 | Fed. Rep. of Germany . |
| 2740849 | 3/1979 | Fed. Rep. of Germany . |
| 2848495 | 5/1979 | Fed. Rep. of Germany . |
| 2827101 | 1/1980 | Fed. Rep. of Germany . |
| 54-34723 | 10/1979 | Japan . |

OTHER PUBLICATIONS

Roedig et al., Chem. Ber. 111, 860–868 (1978).

Kondo et al., Tetrahedron Letters, No. 48, pp. 4359–4362 (1976).

Primary Examiner—Ethel G. Love
Attorney, Agent, or Firm—Sprung, Felfe, Horn, Lynch & Kramer

[57] ABSTRACT

A process for the preparation of a styryl-cyclopropanecarboxylic acid ester of the formula $$R^1\text{-C}_6H_3(R^2)\text{-C}(R^3)=\text{CH}-\text{C}(CH_3)_2\text{-CO}_2R$$

in which
R is $C_{1-4}$-alkyl or an alcohol radical customary in pyrethroids,
$R^1$ is alkoxy or alkylthio, either of which may be optionally substituted by halogen,
$R^2$ is hydrogen or alkoxy, or
$R^1$ and $R^2$ together are optionally halogen-substituted alkylenedioxy, and
$R^3$ is hydrogen or chlorine, comprising reacting a compound of the formula $$R^1\text{-C}_6H_3(R^2)\text{-C}(R^3)=\text{CH}-\text{CHCl}-\text{C}(CH_3)_2-\text{CH}_2\text{CO}_2R$$

$$R^1\text{-C}_6H_3(R^2)\text{-CCl}_2-\text{CH}_2-\text{CHCl}-\text{C}(CH_3)_2-\text{CH}_2-\text{CO}_2R$$

or $$R^1\text{-C}_6H_3(R^2)\text{-CCl}_2-\text{CH}_2-\text{CHCl}-\text{C}(CH_3)_2-\text{CH}_2-\text{CO}-\text{Cl}$$

with, respectively, one, two or three equivalents of a base at a temperature below 60° C. The products are insecticidally active when R is the residue of a pyrethroid-type alcohol. Various syntheses are given for the starting materials which are new.

4 Claims, No Drawings

PROCESS FOR THE PREPARATION OF STYRYL-CYCLOPROPANECARBOXYLIC ACID ESTERS AND INTERMEDIATE PRODUCTS FOR THIS PROCESS

The present invention relates to an unobvious process for the preparation of certain styryl-cyclopropane-carboxylic acid esters, and to new intermediate products for carrying out this process and their preparation.

It has already been disclosed that certain esters of 3-styryl-2,2-dimethylcyclopropanecarboxylic acids have insecticidal properties (German Offenlegungsschrift (German Published Specification) 2,738,150). They are prepared by linking the C-C double bond of the styryl group by a Wittig reaction, in which butyl-lithium is used as the base and which must be carried out at −78° C. under an inert gas. This synthesis route is not practical for an industrial preparation.

Furthermore, the 2,2-dimethyl-3-formyl-1-carboxylic acid ester used as the starting material for this reaction is available industrially only with difficulty.

1. The present invention now provides a process for the preparation of a styryl-cyclopropane-carboxylic acid ester of the general formula

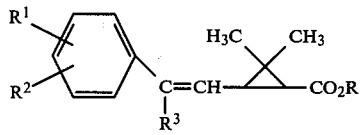
(I)

in which
R represents $C_{1-4}$-alkyl or an alcohol radical customary in pyrethroids,
$R^1$ represents alkoxy or alkylthio, either of which may be optionally substituted by halogen,
$R^2$ represents hydrogen or alkoxy, or
$R^1$ and $R^2$ together represent optionally halogen-substituted alkylenedioxy and
$R^3$ represents hydrogen or chlorine, in which (a) a compound of the general formula

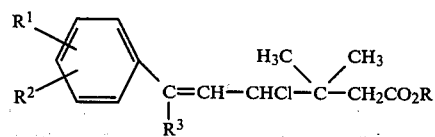
(II)

or (b) a compound of the general formula

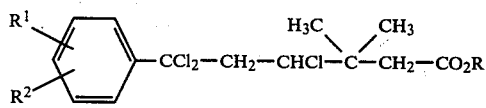
(III)

or (c) a compound of the general formula

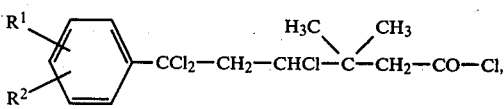
(IV)

in which formulae
$R^1$, $R^2$, $R^3$ and R have the meanings indicated above, is reacted with, respectively, one, two or three equivalents of a base, if appropriate in the presence of a diluent, between −20° C. and +60° C.

2. It has furthermore been found that the compounds of the formula (I) are preferably obtained when the reaction is carried out below 50° C.

3. The compounds of the general formula (II) in which
R, $R^1$, $R^2$ and $R^3$ have the meanings indicated above, are new.

4. The compounds of the general formula (III) in which
$R^1$, $R^2$ and R have the meanings indicated under 1. (above), are new.

5. The compounds of the general formula (IV) in which
$R^1$ and $R^2$ have the meanings indicated above, are new.

6. A process has also been found for the preparation of a compound of the general formula (II), which is characterised in that (a) hydrogen chloride is split off from a compound of the formula (III) by the action of heat, or (b) a compound of the formula (IV) is reacted with an alcohol of the general formula

R—OH         (XIII), in which
R has the meaning indicated under 1, or (c) a compound of the general formula

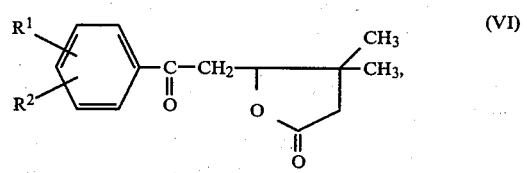
(VI)

in which
$R^1$ and $R^2$ have the meanings indicated above, is reacted with at least two equivalents of phosphorus pentachloride, and the resulting reaction solution is then reacted with an alcohol of the general formula

R—OH         (XIII), in which
R has the meaning indicated under 1, or (d) a compound of the general formula

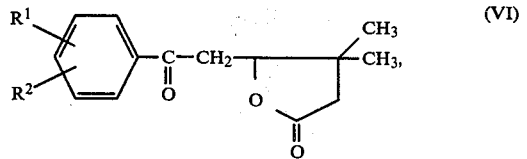
(VI)

in which
$R^1$ and $R^2$ have the meanings indicated above, is reduced, water is split off from the compound obtained and the product is reacted with a chlorinating agent in the presence of an alcohol of the formula (XIII), R therein having the meaning indicated above, or, successively, the lactone ring is first opened with a chlorinating agent and the product is then reacted with the alcohol.

7. A process has also been found for the preparation of a compound of the general formula (III), which is characterized in that a compound of the general formula

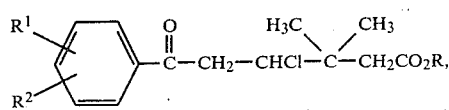
(V)

in which
R¹, R² and R have the meanings indicated under 1. (above), is reacted with phosphorus pentachloride in a diluent below 30° C.

8. A process has also been found for the preparation of a compound of the general formula (IV), characterized in that a compound of the general formula

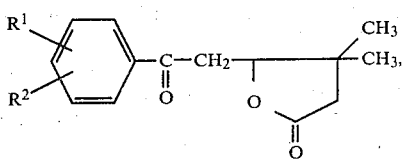
(VI)

in which
R¹ and R² have the meanings indicated above, is reacted with at least two equivalents of phosphorus pentachloride in a diluent below 30° C.

9. The compounds of the formula (V) in which R¹, R² and R have the meanings indicated under 1. (above), are new.

10. A process has also been found for the preparation of a compound of the general formula (V), characterized in that a compound of the formula (VI) is reacted with a chlorinating agent in the presence of an alcohol of the formula (XIII), R therein having the meaning indicated under 1, or, successively, the lactone ring is first opened with a chlorinating agent and the product is then reacted with the alcohol.

11. The new compounds of the general formula (VI) in which
R¹ and R² have the meanings indicated above, have also been found.

12. A process has also been found for the preparation of a compound of the general formula (VI), characterized in that a compound of the general formula

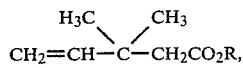
(VII)

in which
R denotes C₁-C₄-alkyl, is reacted with a compound of the general formula

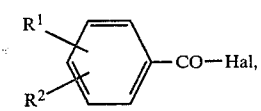
(VIII)

in which
R¹ and R² have the meanings indicated under 1 and Hal denotes halogen, preferably chlorine, in the presence of a Friedel-Crafts catalyst.

13. It has also been found that a compound of the general formula

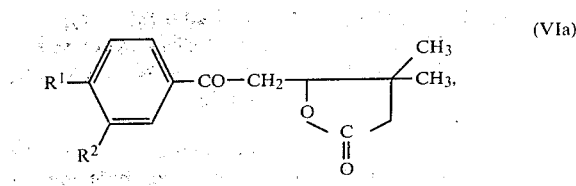
(VIa)

in which
R¹ represents alkoxy or alkylthio and
R² represents hydrogen or alkoxy or, together with R¹, alkylenedioxy, is obtained by a process in which a compound of the general formula

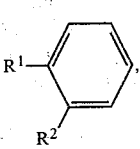
(X)

in which
R¹ and R² have the meanings indicated above, is reacted with the acid chloride of the formula

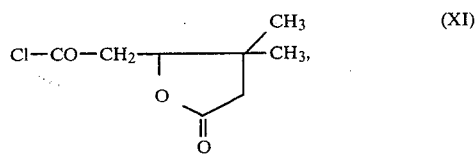
(XI)

in the presence of a Friedel-Crafts catalyst and, if appropriate, in the presence of a diluent.

14. The compound of the formula (XI) is prepared by a process in which the compound of the formula

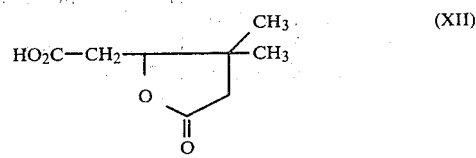
(XII)

is reacted with a chlorinating agent.

The styrylcyclopropanecarboxylic acid esters of the formula (I), which contain a radical of an alcohol customary in pyrethroids and which can be prepared by process 1 according to the invention, have an arthropodicidal, especially an insecticidal and acaricidal, action. Preferably, process 1 is employed for the preparation of styryl-cyclopropanecarboxylic acid derivatives of the formula (I)
in which
R¹ represents C₁-C₄-alkoxy, C₁-C₄-alkylthio, C₁-C₂-fluoroalkoxy, C₁-C₂-chlorofluoroalkoxy or C₁-C₂-fluoroalkylthio,
R² represents hydrogen or methoxy or, together with R¹, C₁-C₂-alkylenedioxy or C₁-C₂-fluoroalkylenedioxy,
R³ represents chlorine and
R represents C₁-C₄-alkyl or the radical of an optionally substituted phenoxybenzyl alcohol of the general formula (XIII)

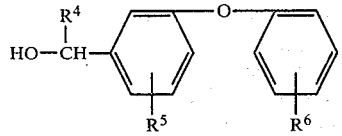

wherein
R⁴ represents hydrogen, cyano or ethynyl and
R⁵ and R⁶ represent hydrogen or fluorine. If 6-(4'-methoxy-phenyl)-4,6-dichloro-3,3-dimethylhex-5-enoic acid ethyl ester is used as the starting material in process variant 1(a), the course of the reaction can be illustrated by the following equation.

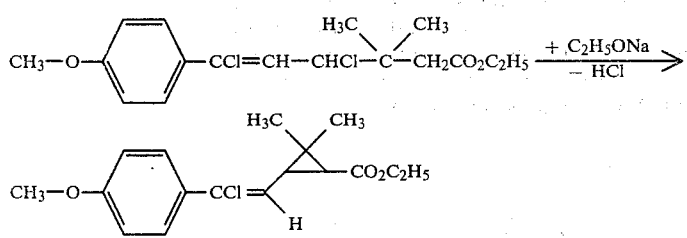

The general formula (II) provides a definition of the starting materials which can be used in process variant 1(a). In this formula, R, R¹ and R² preferably represent the radicals indicated above as preferred and R³ represents chlorine.

The compounds of the formula (II) have not hitherto been disclosed in the literature; their preparation is described below.

If 6-(4'-methoxy-phenyl)-4,6,6-trichloro-3,3-dimethylhexanoic acid methyl ester is used as the starting material in process variant 1(b), the course of the reaction can be illustrated by the following equation:

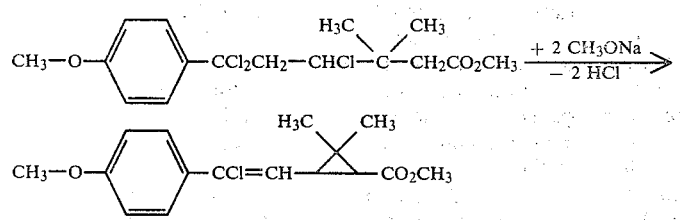

The general formula (III) provides a definition of the starting materials which can be used in process variant 1(b). The preferred substituents R¹, R² and R are the same as those indicated above. The compounds of the formula (III) have not hitherto been disclosed in the literature; their preparation is described below.

If 6-(4'-methoxy-phenyl)-4,6,6-trichloro-3,3-dimethylhexanoic acid chloride is used as the starting material in process 1(c), the course of the reaction can be illustrated by the following equation:

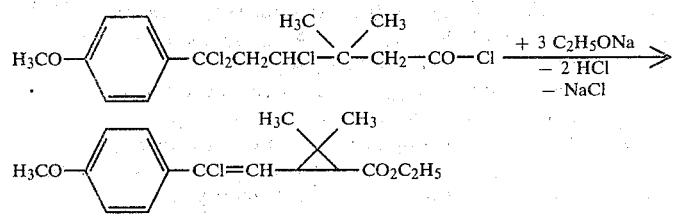

The general formula (IV) provides a definition of the starting materials which can be used in process variant 1(c). The preferred substituents R¹ and R² are the same as those indicated above. The compounds of the formula (IV) have not hitherto been disclosed in the literature; their preparation is described below.

Process variants 1(a), (b) and (c) are carried out by reacting the starting substances (II), (III) and (IV) with, respectively, 1, 2 or 3 equivalents of a base, if appropriate in the presence of a diluent.

An alcoholate, such as sodium methylate, potassium ethylate, sodium ethylate, sodium isopropylate, sodium tert.-butyrate or potassium tert.-butyrate is preferably used as the base.

The alcohol corresponding to the base is preferably employed as the diluent, but other inert diluents, for examplE hydrocarbons, such as toluene, xylene or cyclohexane, or chlorinated hydrocarbons, such as chlorobenzene, or ethers, such as diisopropyl ether, tetrahydrofuran or dioxane, can also be used, additionally or exclusively.

The process is carried out at a temperature between $-20°$ C. and $+60°$ C., preferably between 20° C. and 50° C.

A similar reaction is described in DE-OS (German Published Specification) 2,539,896. However, while the temperature range preferred in this publication is between 60° and 100° C. (page 31) when sodium methylate or sodium ethylate is used, only very little product of the formula (I) is obtained under these conditions, but a further mol of hydrogen halide is predominantly split off, a triple bond being formed.

Surprisingly, it has been found that this can be avoided if the reaction is carried out below 60° C.

Another advantage of the process according to the invention is that only one of the 4 possible stereoisomers is very preferentially formed. It has the trans-configuration, relative to the cyclopropane ring.

The insecticidal and acaricidal esters of this isomeric configuration display a particularly good activity.

The following cyclopropanecarboxylic acid esters of the formula (I) are preferably prepared by process 1: 2,2-dimethyl-3-[2'-chloro-2'-(4''-trifluoromethylmercaptophenyl)-vinyl]-cyclopropane-1-carboxylic acid methyl ester and ethyl ester, 2,2-dimethyl-3-[2'-chloro-2'-(3'',4''-dimethoxy-phenyl)-vinyl]-cyclopropane-1-carboxylic acid methyl ester and ethyl ester, 2,2-dimethyl-3-[2'-chloro-2'-(4''-bromo-phenyl)-vinyl]-cyclopropane-1-carboxylic acid methyl ester and ethyl ester, 2,2-dimethyl-3-[2'chloro-2'-(3'',4''-trifluoroethylenedioxy-phenyl)-vinyl]-cyclopropane-1-carboxylic acid methyl ester and ethyl ester, 2,2-dimethyl-3-[2'-chloro-2'-(3''-trifluoromethylmercapto-phenyl)-vinyl]-cyclopropane-1-carboxylic acid methyl ester and ethyl ester, 2,2-dimethyl-3-[2'-chloro-2'-(4''-methylmercaptophenyl)-vinyl]-cyclopropane-1-carboxylic acid methyl ester and ethyl ester, 2,2-dimethyl-3-[2'-chloro-2'-(4''-ethoxy-phenyl)-vinyl]-cyclopropane-1-carboxylic acid methyl ester and ethyl ester, 2,2-dimethyl-3-[2'-chloro-2'-(4''-methoxy-phenyl)-vinyl]-cyclopropane-1-carboxylic acid methyl ester and ethyl ester, 2,2-dimethyl-3-[2'-chloro-2'-(4''-trifluoromethoxyphenyl)-vinyl]-cyclopropane-1-carboxylic acid methyl ester and ethyl ester, 2,2-dimethyl-3-[2'-chloro-2'-(3''-trifluoromethoxy-4''-chloro-phenyl)-vinyl]-cyclopropane-1-carboxylic acid methyl ester and ethyl ester and 2,2-dimethyl-3-(2'-chloro-2'-(3'',4''-methylenedioxyphenyl)-vinyl]-cyclopropane-1-carboxylic acid methyl ester and ethyl ester.

The compounds of the general formula (II) are new. They are obtained by the process indicated under 6, by (a) splitting off hydrogen chloride from compounds of the general formula (III) by the action of heat or (b) reacting compounds of the formula (IV) with alcohols, or (c) reacting compounds of the formula (VI) with phosphorus pentachloride and then reacting the product with an alcohol, or (d) reducing compounds of the formula (VI), splitting off water from the compounds obtained and reacting the products with an chlorinating agent in the presence of an alcohol, or, successively, first opening the lactone ring with a chlorinating agent and then reacting the product with an alcohol.

If 6-(4'-methoxy-phenyl)-4,6,6-trichloro-3,3-dimethylhexanoic acid ethyl ester is used as the starting material in process 6(a), the course of the reaction can be represented by the following equation:

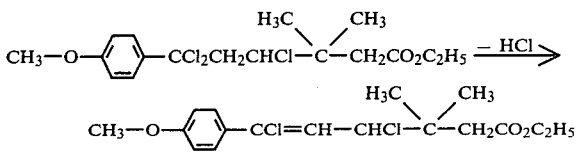

The general formula (III) provides a definition of the starting substances which can be used in process 6(a). The preferred substituents $R^1$, $R^2$ and R are the same as those for process variant 1(a).

The compounds of the formula (III) are new; their preparation is described below.

Process 6(a) is carried out by warming the starting substances of the formula (III), if appropriate in a diluent, to a temperature between 25° and 80° C., preferably to a temperature between 30° and 50° C. During this procedure, hydrogen chloride is split off. Preferred diluents are hydrocarbons, such as benzene, toluene, xylene, benzine, cyclohexane or petroleum ether; chlorinated hydrocarbons, such as methylene chloride, chloroform, carbon tetrachloride, dichloroethane or chlorobenzene; and nitriles, such as acetonitrile.

If appropriate, isolation of the compounds of the general formula (III) can be dispensed with, so that process 6(a) immediately follows process 7 (see below).

If 6-(4'-methoxy-phenyl)-4,6,6-trichloro-3,3-dimethylhexanoic acid chloride is used as the starting substance in process 6(b), the course of the reaction can be represented by the following equation:

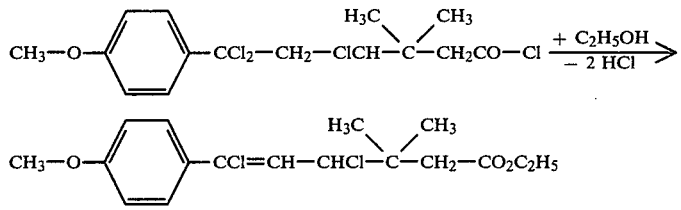

The general formula (IV) provides a definition of the starting substances which can be used in process 6(b). The preferred substituents $R^1$ and $R^2$ are the same as those in the case of process variant 1(a).

The compounds of the formula (IV) are new; their preparation is described below.

Process 6(b) is carried out by adding an alcohol of the general formula R—OH, the preferred meaning of R being the same as that in the case of process variant 1(a), to the starting substance of the formula (IV), if appropriate in a diluent, at a temperature between −20° C. and +80° C., preferably between 0° C. and 30° C. In order to bring the reaction to completion, the mixture is then stirred for a further period at elevated temperature, preferably between 30° and 60° C. Excess alcohol can be used as the diluent, as can any of the solvents which can also be used in process 6(a).

If 3,3-dimethyl-4-(4'-methoxy-phenacyl)-γ-butyrolactone and ethanol are used as starting substances in process 6(c), the course of the reaction can be represented by the following equation:

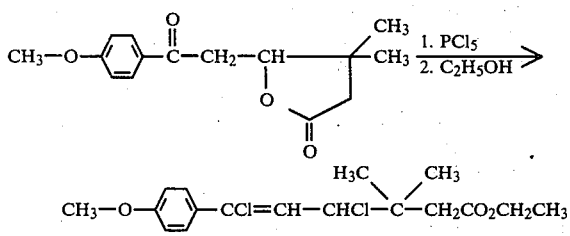

The general formula (VI) provides a definition of the starting substances which can be used in process 6(c). The preferred substituents $R^1$ and $R^2$ are the same as those in the case of process variant 1(a). The compounds of the formula (VI) are new; their preparation is described below.

Phosphorus pentachloride can be used as the chlorinating agent.

Process 6(c) is carried out by a procedure in which the starting substance of the general formula (VI) is initially introduced and is reacted with at least two equivalents of the chlorinating agent. A slight excess is favorable.

In contrast to the generally customary procedure (Houben-Weyl, volume V, 3, page 912 et seq.) for the reaction of ketones with phosphorus pentachloride, the process is preferably carried out in the presence of a diluent. Preferred diluents are the same as those mentioned for process 6(a).

Using a diluent and metering in the phosphorus pentachloride, it is possible, surprisingly, to avoid the otherwise customary side reactions, for example chlorination in the α-position relative to the carbonyl group or addition of hydrogen chloride onto the chlorovinyl group.

The reaction temperature is between −20° C. and +60° C., preferably between 0° C. and 35° C.

Subsequent esterification is effected by adding excess alcohol R-OH dropwise, analogously to process 6(b).

The mixture is worked up by washing the organic phase until neutral and separating it off, and distilling off the solvent and the phosphoric acid ester. Purification by distillation at this stage can usually be dispensed with.

If 3,3-dimethyl-4-(methoxy-phenacyl)-γ-butyrolactone is used as the starting material in process 6(d), the course of the reaction can be represented by the following equation:

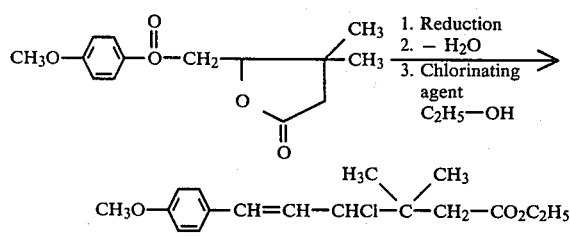

The general formula (VI) provides a definition of the starting substances which can be used in process 6(d). The preferred and particularly preferred substituents $R^1$ and $R^2$ are the same as those in the case of process variant 1(a). The compounds of the formula (VI) are new; their preparation is described below.

In principle, any of the agents by which a ketone is reduced to the alcohol without the lactone ring being attacked can be used as the reducing agent. Examples which may be mentioned are: a complex borohydride, such as sodium borohydride, or hydrogen in the presence of, for example, a nickel catalyst, palladium catalyst or platinum catalyst, such as Raney nickel. Sodium borohydride is preferred.

Process 6(d) is carried out by a procedure in which, after the reducing step, which is carried out in a manner which is in itself customary, the product is dehydrated, that is to say water is split off.

An acid catalyst is preferably employed for the dehydration. Examples which may be mentioned are: oxalic acid, sulphuric acid, phosphoric acid, potassium bisulphate, p-toluenesulphonic acid, aluminum oxide and silicates. In addition, it is possible to split off acetic acid by heating after acetylation of the alcohol. The acetylation is carried out with acetyl chloride or acetic anhydride. The third step of process 6(d) corresponds to process 10 (see below).

If 6-(3′-methoxy-phenyl)-6-oxo-4-chloro-3,3-dimethylhexanoic acid ethyl ester is used as the stating substance in process 7, the course of the reaction can be represented by the following equation:

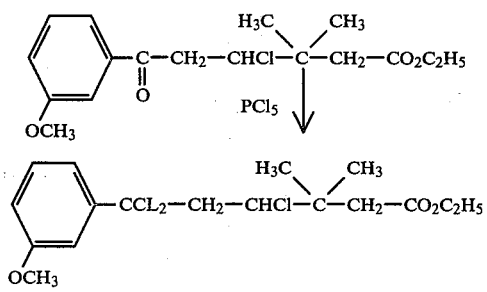

The general formula (V) provides a definition of the starting substances which can be used in process 7. The preferred substituents $R^1$, $R^2$ and R are the same as those in the case of process variant 1(a). The compounds of the formula (V) are new; their preparation is described below.

It has been found that the compounds (III) are obtained from the compounds of the formula (V) only when the reaction is carried out in a diluent below 30° C.

Process 7 is carried out by a procedure in which the starting substance of the general formula (V) is dissolved in a diluent. Preferred diluents are the same as those mentioned for process 6(a), especially petroleum ether, cyclohexane, toluene and chlorobenzene.

The reaction temperature is between −20° C. and +30° C., preferably between 0° and 25° C.

The mixture is worked up by adding ice-water, washing the organic phase until neutral and distilling off the solvent.

The structure is proved by a nuclear magnetic resonance spectrum.

If 3,3-dimethyl-4-(4′-methoxy-phenacyl)-γ-butyrolactone is used as the starting substance in process 8, the course of the reduction can be represented by the following equation:

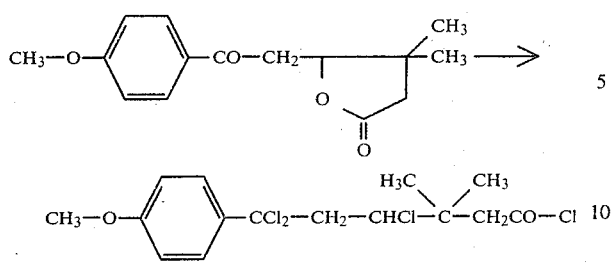

The general formula (VI) provides a definition of the starting substances which can be used in process 8. The preferred substituents are the same as in the case of process 1(a). The compounds of the formula (VI) are new; their preparation is described below.

It has furthermore been found that the compounds (IV) are obtained from the compounds (VI) only if the reaction is carried out in a diluent below 30° C.

Process 8 is carried out by a procedure in which the starting substance of the general formula (VI) is dissolved in a diluent.

Preferred diluents are the same as those mentioned for process 6(a), especially petroleum ether, cyclohexane, toluene and chlorobenzene.

The reaction temperature is between −20° and +30° C., preferably between 0° and 25° C.

The compounds of the formula (IV) can be isolated by distilling off the solvent and phosphorus oxychloride under gentle conditions, or they can be directly reacted further according to process variant 1(c) or process 6(b).

If 3,3-dimethyl-4-(4'-methoxy-phenacyl)-γ-butyrolactone and ethanol are used as starting substances in process 10, the course of the reaction can be represented by the following equation:

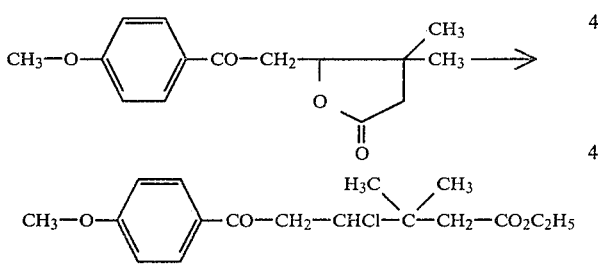

The general formula (VI) provides a definition of the starting substances which can be used in process 10. The preferred substituents $R^1$ and $R^2$ are the same as those in the case of process variant 1(a). The compounds of the formula (VI) are new; their preparation is described below.

The second starting substance for process 10 is an alcohol of the formula R-OH, the preferred meaning of R being the same as that in the case of process variant 1(a).

The following chlorinating agents can be used in process 10: hydrogen chloride, thionyl chloride, phosgene or phosphorus trichloride, and hydrogen chloride and thionyl chloride are preferred; if appropriate, dimethylformamide is used as a catalyst.

Lactone ring openings of this type are known in principle, but in no case do such lactones contain an additional carbonyl group. Conditions therefore had to be found to achieve a process in which only the desired reaction proceeds and not, for example, (1) acid-catalyzed self-condensations of the ketone (acetophenone, for example, reacts with itself in this manner under catalysis by hydrogen chloride) and (2) chlorination of the carbonyl group or of the hydrogen atoms in the α-position relative to the carbonyl group.

Process 10 is carried out by a procedure in which the starting substance of the formula (VI) is dissolved in an alcohol of the formula R-OH, if appropriate a diluent is also added and the chlorinating agent is then passed in or added dropwise. An exothermic reaction starts; in order to avoid the above-mentioned side reactions, the temperature should in no case exceed 80° C., but the reaction is preferably carried out between 20° and 50° C.

Preferred diluents are, in particular, benzene, toluene, benzine, petroleum ether, cyclohexane, chlorobenzene or xylene.

In principle, it is also possible first to open the lactone ring and then to add the alcohol. In this case, the starting compound (VI), if appropriate in one of the diluents mentioned, is heated to temperatures between 50° and 80° C. (higher temperatures are not appropriate), a chlorinating agent being added, if appropriate under pressure. The alcohol R-OH is then added dropwise or pumped in.

The resultant compound of the formula (V) is isolated by distilling off the solvent under gentle conditions. Further purification is difficult, but also unnecessary. The crude compounds of the formula (V) can be used directly for process 7.

If 3,3-dimethyl-pent-4-enoic acid methyl ester and p-methoxy-benzoyl chloride are used as starting substances in process 12, the course of the reaction can be represented by the following equation:

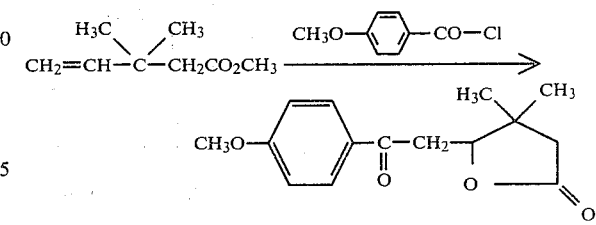

The general formulae (VII) and (VIII) provide definitions of the starting substances which can be used in process 12. The preferred substituents $R^1$, $R^2$ and $R^3$ are the same as those in the case of process 1(a). The compounds of the formula (VII) (DT-OS (German Published Specification) 2,539,895) and (VIII) are known.

Examples of compounds of the formula (VIII) are: 4-methoxybenzoyl chloride, 4-trifluoromethoxy-benzoyl chloride, 3-trifluoromethylmercapto-benzoyl chloride, 3-trifluoromethoxy-4-chlorobenzoyl chloride, 3,4-methylenedioxy-benzoyl chloride, 3,4-dimethoxybenzoyl chloride, 4-trifluoromethylmercapto-benzoyl chloride, 4-ethoxybenzoyl chloride and 3,4-trifluoroethylenedioxy-benzoyl chloride.

Possible catalysts are Friedel-Crafts catalysts. The particularly preferred catalyst is tin tetrachloride, or, if appropriate, mixtures containing aluminum chloride, titanium tetrachloride, zinc chloride or iron(III) chloride. If aluminum chloride is used by itself, the compounds formed are not those of the formula (VI) but those of the formula (V). The Friedel-Crafts catalyst is employed in an equimolar amount or in an amount which is less than or more than the equimolar amount. Process 12 can be carried out with or without a diluent. If a diluent is used, possible diluents are methylene chloride, chloroform, dichloroethane, tetrachloroethane, nitromethane or nitrobenzene.

The process according to the invention is carried out by a procedure in which the Friedel-Crafts catalyst, if appropriate in a diluent, is initially introduced and the acid halide of the general formula (VIII) is added, while cooling. An ester of the general formula (VII) is then added dropwise at temperatures between $-25°$ C. and $+50°$ C., preferably at temperatures between $0°$ C. and $25°$ C.

However, it is also possible to initially introduce an acid halide of the formula (VIII), together with an ester of the formula (VII), if appropriate in the presence of a diluent, and then to meter in the Friedel-Crafts catalyst.

To accelerate the reaction, when mixing of the reactants has ended, the reaction can be carried out at elevated temperature, for example at $25°$ to $150°$ C., preferably at $30°$ to $100°$ C. The end of the reaction can be recognized by the end of the evolution of gas. After rendering the mixture acid, it is worked up in the customary manner by extraction. The crude product of the general formula (VI) can be purified by recrystallization.

The course of the reaction is extremely surprising, since lactone formation under conditions which are so mild was hitherto unknown.

If anisole and 3,3-dimethyl-4-chlorocarbonylmethyl-γ-butyrolactone are used as starting substances in process 13 for the preparation of the compounds of the formula (VI), the course of the reaction can be represented by the following equation:

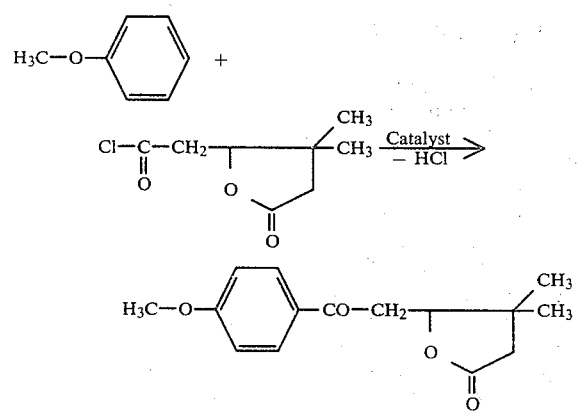

The formula (X) and (XI) provide definitions of the starting substances which can be used in process 13. The compound (XI) is new; its preparation is described below.

The compounds of the formula (X) are known, and examples which may be mentioned are: ethoxybenzene, methylmercaptobenzene, anisole, benzodioxole and pyrocatechol dimethyl ether. Possible catalysts are in principle any of the customary Friedel-Crafts catalysts, such as aluminum chloride, tin tetrachloride, titanium tetrachloride, hydrogen fluoride, boron trifluoride, iron(III) chloride, zinc chloride, polyphosphoric acids, perfluoroalkanesulphonic acids (optionally in polymeric form) and optionally mixtures thereof.

The process is preferably carried out in the presence of a diluent. Possible diluents are: methylene chloride, chloroform, dichloroethane, tetrachloroethane, nitrobenzene and nitromethane. Methylene chloride is preferred.

The reaction is extremely surprising, since it had to be expected that the lactone ring would also react, in the following manner:

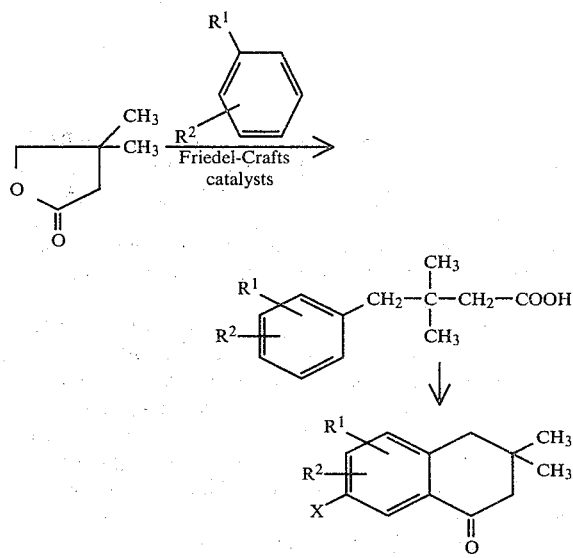

and in addition cyclization to give the tetralone was to be expected. Ring openings of 5-membered lactone rings using aromatics by a Friedel-Crafts reaction in the manner formulated above are known and take place under very mild conditions (Houben-Weyl; volume VI, 2, page 812 et seq.).

That such a reaction of the lactone with the aromatics of the formula (X) does not take place is also surprising, especially since the Friedel-Crafts catalyst must be employed in at least an equimolar amount, and even better in excess.

Process 13 is preferably carried out as follows:

The acid chloride (XI) is initially introduced in a diluent, and the Friedel-Crafts catalyst is added at a temperature between $-10°$ and $+5°$ C. The aromatic compound is then added dropwise, if appropriate likewise dissolved in a diluent. If very active Friedel-Crafts catalysts (for example aluminum chloride or tin tetrachloride) are used, this procedure is carried out at $-10°$ to $+5°$ C., and in the case of less active Friedel-Crafts catalysts (for example zinc chloride, iron chloride, titanium tetrachloride or perfluoroalkanesulphonic acids), the aromatic compounds are added dropwise at room temperature. The mixture is then subsequently stirred at room temperature; in the case of less active catalysts the reaction must be carried out at elevated temperature if necessary.

If aromatics which are slow to react, for example chlorobenzene, are used, it is advisable not to accelerate the reaction by increasing the temperature but to extend the reaction times in order to prevent undesired lactone ring opening in the above-mentioned sense.

The mixture is worked up in the customary manner; the lactones can be purified by recrystallization.

Process 14 can be represented by the following equation:

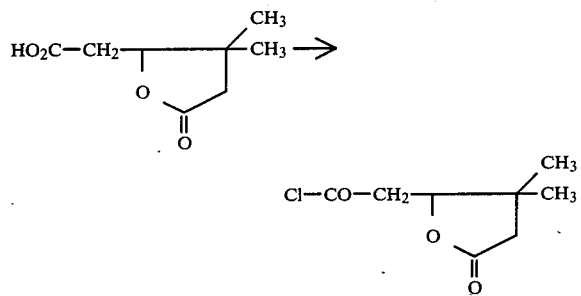

The acid of the formula (XII) used as the starting substance is known (J. Org. Chem., volume 38, page 4148 and J. Chem. Soc. 79, 763), but the acid chloride of the formula (XI) is not. It appears surprising that the acid is converted smoothly into the acid chloride, since under these conditions ring opening of the lactone usually also takes place.

Process 14 is carried out under the conditions which are customary for preparing an acid chloride from an acid. Preferred chlorinating agents are thionyl chloride and phosgene. However, care must be taken that reaction times which are as short as possible are applied, in order to avoid a side reaction in the above-mentioned sense. The mixture is worked up in the customary manner. The acid chloride can be purified by distillation or can be employed in the crude form in process 13.

The styrylcyclopropanecarboxylic acid esters of the formula (I) which contain a radical of an alcohol customary in pyrethroids are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber*;

from the class of the Diplopoda, for example *Blaniulus guttulatus*;

from the class of the Chilopoda, for example *Geophilus carpophagus* and *Scutigera* spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria*;

from the order of the Dermaptera, for example *Forficula auricularia*;

from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci*;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*;

from the order of the Siphonaptera, for example *Xenopsylla cheopis* and Ceratophyllus spp.;

from the class of the Arachnida, for example *Scorpio maurus* and *Latrodectus mactans*;

from the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The invention is further described in the following illustrative examples:

EXAMPLE 1

(process variant 1(a))

A solution of sodium ethylate (prepared from 2.5 g of sodium and 100 ml of ethanol) was added dropwise to a solution of 34.5 g (0.1 mol) of 6-(4'-methoxy-phenyl)-4,6-dichloro-3,3-dimethyl-hex-5-enoic acid ethyl ester in 100 ml of ethanol at room temperature. The mixture was subsequently stirred for 4 hours, diluted with ice-water and rendered neutral. After extraction with methylene chloride, the organic phase was dried and concentrated on a rotary evaporator. Distillation under a high vacuum gave 26.5 g of a pale yellowish oil of boiling point 162°–168° C./0.08 mbar. It contained all the 4 possible stereoisomers of 2,2-dimethyl-3-[2'-chloro-2'-(4''-methoxy-phenyl)]-vinyl-cyclopropane-1-carboxylic acid ethyl ester. The vinyl proton of the main isomers showed (in CDCl$_3$) a doublet at $\delta = 5.7$ and 5.85 ppm. Mass spectrum: m/e = 308.

EXAMPLE 2

(process variant 1(b))

A solution of 38.2 g of 6-(4'-methoxy-phenyl)-4,6,6-trichloro-3,3-dimethyl-hexanoic acid ethyl ester (crude; from Example 8) in 100 ml of ethanol was added dropwise to a solution of 4.75 g of sodium in 250 ml of ethanol at room temperature. The mixture was subsequently stirred at room temperature for 2 hours and then heated to 50° C. for a further 1 hour. Ice-water was then added and the mixture was neutralized with 10% strength hydrochloric acid. After extraction twice with methylene chloride, the organic phases were dried and concentrated on a rotary evaporator and the residue was distilled under a high vacuum. 25 g of 2,2-dimethyl-3-[2'-chloro-2'-(4''-methoxy-phenyl)]-vinyl-cyclopropane-1-carboxylic acid ethyl ester of boiling point 155°–163° C./0.05 mbar were obtained.

EXAMPLE 3

(process variant 1(c))

A solution of 40 g of sodium in 700 ml of ethanol was added to a solution of 35 g of 6-(4'-methoxy-phenyl)-4,6,6-trichloro-3,3-dimethyl-hexanoic acid chloride (crude, still containing POCl₃; from Example 9) in 500 ml of toluene, while cooling with ice. The mixture was stirred at room temperature for 8 hours and then heated to 50° C. for a further 1 hour, ice-water was added, the mixture was neutralized with 10% strength hydrochloric acid, the toluene phase was separated off and the aqueous phase was washed with methylene chloride. The combined organic phases were dried and the solvents and the phosphoric acid triethyl ester formed were distilled off. The residue was purified by distillation under a high vacuum. 18.6 g of 2,2-dimethyl-3-[2'-chloro-2'-(4''-methoxy-phenyl)]-vinylcyclopropane-1-carboxylic acid ethyl ester were obtained.

EXAMPLE 4

(process variant 1(c))

2,2-Dimethyl-3-[2'-chloro-2'-(4''-methylmercapto-phenyl)]-vinylcyclopropane-1-carboxylic acid ethyl ester was obtained from 6-(4''-methylmercaptophenyl)-4,6,6-trichloro-3,3-dimethyl-hexanoic acid chloride and sodium ethylate analogously to Example 3.

EXAMPLE 5

(process 6(a))

A solution of 6-(4'-methoxy-phenyl)-4,6,6-trichloro-3,3-dimethyl-hexanoic acid methyl ester in toluene was warmed to about 40° C. for 1 hour. After distilling off the toluene in vacuo, 6-(4'-methoxy-phenyl)-4,6-dichloro-3,3-dimethyl-hex-5-enoic acid methyl ester remained. The structure was proved by the NMR spectrum.

EXAMPLE 6

(process 6(b))

20 times the equimolar amount of dry methanol was added to a solution of 6-(4'-methoxy-phenyl)-4,6,6-trichloro-3,3-dimethyl-hexanecarboxylic acid chloride (crude still contained POCl₃; from Example 9) in toluene at 20° C. and the mixture was then warmed to 40° C. for a further 1 hour. After subsequently stirring the mixture for 4 hours (without heating) the solvents and the phosphoric acid ester were removed in vacuo. The residue was identical to the product obtained in Example 5.

EXAMPLE 7

(process variant (6(c))

46 g of phosphorus pentachloride were added to a solution of 26.2 g of 3,3-dimethyl-4-(4'-methoxy-phenacyl)-γ-butyrolactone in 400 ml of toluene and the mixture was stirred at room temperature until all the PCl₅ had dissolved. 120 ml of ethanol were then added dropwise at 20° C. and thereafter the mixture was warmed to 45° C. for 1 hour and subsequently stirred further until it reached room temperature again. It was then poured into a large amount of ice-water and rendered neutral. The toluene phase was separated off, dried and concentrated in a rotary evaporator. After distilling off the solvent and the phosphoric acid triethyl ester, 25 g of a dark oil which consisted mainly of 6-(4'-methoxy-phenyl)-4,6-dichloro-3,3-dimethyl-hex-5-enoic acid ethyl ester and which could be further processed according to process variant 1(a) (Example 1) remained.

EXAMPLE 8

(process 7)

7.9 g of 6-(4'-methoxy-phenyl)-6-oxo-4-chloro-3,3-dimethyl-hexanoic acid ethyl ester were dissolved in 50 ml of toluene, and 6 g of phosphorus pentachloride were added at room temperature. The mixture was subsequently stirred at room temperature for 9 hours, poured into 100 ml of ice-water and rendered neutral and the toluene phase was separated off. After drying the toluene phase and distilling off the toluene at room temperature, 68 g of an oil which, according to the NMR spectrum, consisted of 6-(4'-methoxy-phenyl)-4,6,6-trichloro-3,3-dimethyl-hexanoic acid ethyl ester remained. The oil could be reacted further according to process variant 1(b).

EXAMPLE 9

(process 8)

26.2 g of 3,3-dimethyl-4-(4'-methoxy-phenacyl)-γ-butyrolactone were dissolved in 500 g of toluene, and 46 g of phosphorus pentachloride were added. The mixture was subsequently stirred at room temperature for 18 hours and phosphorus oxychloride and toluene were then distilled off at room temperature in vacuo. 37 g of a brown oil which was identified as 6-(4'-methoxy-phenyl)-4,6,6-trichloro-3,3-dimethyl-hexanecarboxylic acid chloride by IR and NMR remained.

EXAMPLE 10

(process 11)

78.6 g of 3,3-dimethyl-4-(4'-methoxy-phenacyl)-γ-butyrolactone were dissolved in 500 ml of ethanol, and dry hydrogen chloride was passed in until the temperature had reached 50° C. A slow stream of hydrogen chloride was then passed through the solution at 50° C., initially while cooling, for 3 hours, and then continued to be passed in until the mixture reached room temperature again. Distilling off the ethanol in vacuo gave 98 g of 6-(4'-methoxy-phenyl)-6-oxo-4-chloro-3,3-dimethyl-hexanoic acid ethyl ester.

EXAMPLE 11

(process 11)

131 g of 3,3-dimethyl-4-(4'-methoxy-phenacyl)-γ-butyrolactone were dissolved in 215 g of thionyl chloride in a 0.7 liter autoclave with a glass liner. 100 g of ethanol were then pumped in and the mixture was kept at 50° C. for 4 hours. After cooling and letting down, excess thionyl chloride and sulphurous acid ethyl ester were distilled off. The residue essentially consisted of 6-(4'-methoxy-phenyl)-6-oxo-4-chloro-3,3-dimethyl-hexanoic acid ethyl ester.

EXAMPLE 12

(process 11)

131 g of 3,3-dimethyl-4-(4'-methoxy-phenacyl)-γ-butryolactone were dissolved in 215 g of thionyl chloride in a 0.7 liter autoclave with a glass liner. 100 g of methanol were then pumped in and the mixture was heated to 50° C. for 4 hours. After working up as in Example 10, 6-(4'-methoxy-phenyl)-6-oxo-4-chloro-3,3-dimethyl-hexanoic acid methyl ester was obtained.

EXAMPLE 13

(process 12)

71 g (0.5 mol) of 3,3-dimethyl-4-pentenoic acid methyl ester were prepared dropwise to a mixture of 85.5 g (0.5 mol) of p-methoxybenzoyl chloride and 130.3 g (0.5 mol) of tin tetrachloride at 20° C., while cooling with ice. After standing overnight, the reaction mixture had solidified. It was taken up in methylene chloride, the methylene chloride mixture was filtered and the filtrate was extracted by shaking with dilute hydrochloric acid. After drying and stripping off the solvent in vacuo, a crude product which crystallized completely was obtained. Recrystallization from ethanol gave 3,3-dimethyl-4-(4'-methoxy-phenacyl)-γ-butryolactone of melting point 132°–134° C.

EXAMPLE 14

(process 12)

26 g (0.1 mol) of tin tetrachloride were added dropwise to a solution of 17.1 g (0.1 mol) of p-methoxybenzoyl chloride and 14.2 g (0.1 mol) of 3,3-dimethyl-4-pentenoic acid methyl ester in 100 ml of methylene chloride at 0° and the mixture was then heated under reflux for 8 hours, until the evolution of gas had ended. After working up with dilute hydrochloric acid, 23.9 g (91%) of 3,3-dimethyl-4-(4'-methoxyphenacyl)-γ-butyrolactone of melting point 132°–134° C. (from ethanol) were obtained.

EXAMPLE 15

(process 14)

17.2 g of 3,3-dimethyl-4-carboxymethyl-γ-butyrolactone were mixed with 60 ml of thionyl chloride and the mixture was heated to 80° C. for 1 hour. Excess thionyl chloride was then distilled off under normal pressure, the last residues under a waterpump vacuum. The residue consisted of 3,3-dimethyl-4-chlorocarbonylmethyl-γ-butyrolactone and could be used directly for process 13. However, it could also be further purified by distillation: boiling point: 130°–140° C./0.3 mbar.

EXAMPLE 16

(process 13)

80 g of aluminum chloride were initially introduced into 300 ml of methylene chloride, and 59 g of 3,3-dimethyl-4-chlorocarbonylmethyl-γ-butyrolactone dissolved in 150 ml of methylene chloride, were added dropwise at 0°–5° C. 32.4 g of anisole, dissolved in 50 ml of methylene chloride, were then added dropwise, likewise at 0°–5° C. The mixture was then allowed to come to room temperature and was subsequently stirred at room temperature for a further 7 hours. After pouring the batch into ice-water, the organic phase was separated off and washed until neutral. After drying the organic phase and distilling off the solvent, crude 3,3-dimethyl-4-(4'-methoxy-phenacyl)-γ-butyrolactone, which was recrystallized from ethanol, was obtained. Melting point: 132°–134° C.

EXAMPLE 17

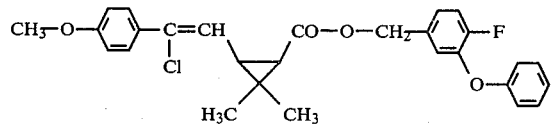

4.4 g (0.02 mol) of 3-phenoxy-4-fluoro-benzyl alcohol and 7.1 g (0.02 mol) of 2,2-dimethyl-3-(2-chloro-2-(4-methoxy-phenyl)-vinyl)-cyclopropanecarboxylic acid chloride were dissolved in 100 ml of anhydrous toluene, and 2.5 g of pyridine, dissolved in 50 ml of anhydrous toluene, were added dropwise at 20°–25° C., while stirring. The mixture was then stirred at 25°–35° C. for a further 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled under a waterpump vacuum. Last residues of solvent were removed by brief incipient distillation at a bath temperature of 60° C./1 mm Hg. 8.1 g (84.5% of theory) of 2,2-dimethyl-3-(2-chloro-2-(4-methoxyphenyl)-vinyl)-cyclopropanecarboxylic acid (4-fluoro-3-phenoxy-benzyl)-ester were obtained.

The following compound was obtained analogously:

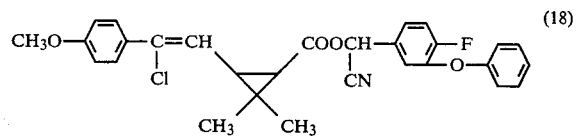

(18)

The pesticidal activity of the compounds of this invention is illustrated by the following example:

EXAMPLE 18

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvea had been killed whereas 0% meant that none of the beetle larvae had been killed.

In this test, for example, the compound of Example 17 showed high activity.

It will be appreciated that the instant specification and examples are set forth by way of illustration and not limitation, and that various modifications and changes may be made without departing from the spirit and scope of the present invention.

We claim:

1. A compound selected from the group consisting of

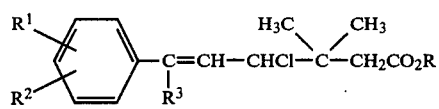

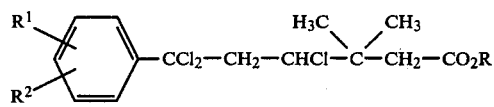

and

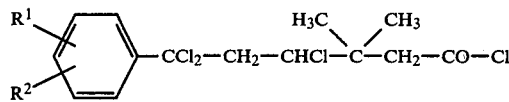

in which
R is $C_{1-4}$-alkyl or,

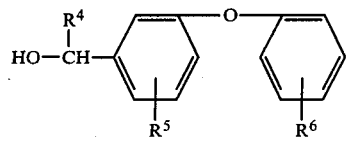

$R^4$ is hydrogen, cyano or ethynyl,
$R^5$ and $R^6$ each independently is hydrogen or fluorine,
$R^1$ is alkoxy or alkylthio, either of which may be optionally substituted by halogen,
$R^2$ is hydrogen or alkoxy, or
$R^1$ and $R^2$ together are optionally halogen-substituted alkylenedioxy, and
$R^3$ is hydrogen or chlorine.

2. A compound according to claim 1, in which said compound is

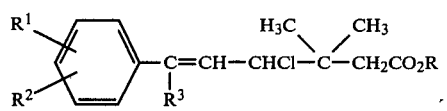

3. A compound according to claim 1, in which said compound is

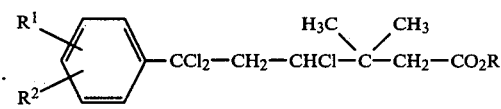

4. A compound according to claim 1, in which said compound is

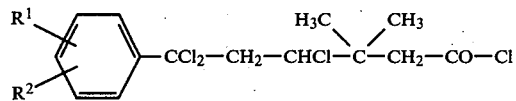

* * * * *